(12) United States Patent
Paulus

(10) Patent No.: US 8,512,329 B2
(45) Date of Patent: Aug. 20, 2013

(54) MICROWAVE ANTENNA ASSEMBLY HAVING A DIELECTRIC BODY PORTION WITH RADIAL PARTITIONS OF DIELECTRIC MATERIAL

(75) Inventor: Joseph A. Paulus, Louisville, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/539,650

(22) Filed: Jul. 2, 2012

(65) Prior Publication Data

US 2012/0271297 A1  Oct. 25, 2012

Related U.S. Application Data

(63) Continuation of application No. 12/197,405, filed on Aug. 25, 2008, now Pat. No. 8,211,098.

(51) Int. Cl.
*A61B 18/04* (2006.01)

(52) U.S. Cl.
USPC .......................................................... 606/33

(58) Field of Classification Search
USPC ............... 606/33, 41, 50; 607/115, 116, 154, 607/156
See application file for complete search history.

(56) References Cited

U.S. PATENT DOCUMENTS

| D223,367 S | 4/1972 | Kountz |
| D263,020 S | 2/1982 | Rau, III |
| D266,842 S | 11/1982 | Villers et al. |
| D278,306 S | 4/1985 | McIntosh |
| 4,658,836 A | 4/1987 | Turner |
| 4,700,716 A | 10/1987 | Kasevich et al. |
| D295,893 S | 5/1988 | Sharkany et al. |
| D295,894 S | 5/1988 | Sharkany et al. |
| 5,375,596 A | 12/1994 | Twiss et al. |
| D354,218 S | 1/1995 | Van de Peer |
| 5,383,889 A | 1/1995 | Warner et al. |
| 5,634,928 A | 6/1997 | Fischell et al. |
| 5,697,927 A | 12/1997 | Imran et al. |
| D424,693 S | 5/2000 | Pruter |
| D424,694 S | 5/2000 | Tetzlaff et al. |
| D425,201 S | 5/2000 | Tetzlaff et al. |
| 6,275,738 B1 | 8/2001 | Kasevich et al. |
| D449,886 S | 10/2001 | Tetzlaff et al. |
| D457,958 S | 5/2002 | Dycus et al. |
| D457,959 S | 5/2002 | Tetzlaff et al. |
| D487,039 S | 2/2004 | Webster et al. |

(Continued)

FOREIGN PATENT DOCUMENTS

| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Aarti B Berdichevsky

(57) ABSTRACT

A microwave antenna assembly includes first and second elongated conductors, and a dielectric body portion. The first elongated conductor is associated with a first radiating portion at least partially along the length thereof. A second elongated conductor is disposed within the first elongated conductor and is associated with a second radiating portion at least partially along the length thereof. The dielectric body portion is disposed along the length of at least one of the first and second elongated conductors and the dielectric body portion includes two or more radial partition of dielectric material having difference dielectric constants.

7 Claims, 6 Drawing Sheets

(56) References Cited

U.S. PATENT DOCUMENTS

| | | |
|---|---|---|
| 6,740,108 B1 | 5/2004 | Just et al. |
| D496,997 S | 10/2004 | Dycus et al. |
| D499,181 S | 11/2004 | Dycus et al. |
| 6,962,587 B2 | 11/2005 | Johnson et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| 7,270,351 B2 | 9/2007 | Chelchowski et al. |
| D564,662 S | 3/2008 | Moses et al. |
| D576,932 S | 9/2008 | Strehler |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 8,070,789 B2 | 12/2011 | Will et al. |
| 8,118,808 B2 | 2/2012 | Smith et al. |
| 8,133,222 B2 | 3/2012 | Ormsby |
| 8,216,226 B2 | 7/2012 | Young et al. |
| 8,216,227 B2 | 7/2012 | Podhajsky |
| 2003/0083654 A1 | 5/2003 | Chin et al. |
| 2003/0109868 A1 | 6/2003 | Chin |
| 2004/0148004 A1 | 7/2004 | Wallsten |
| 2006/0084867 A1 | 4/2006 | Tremblay et al. |
| 2007/0050000 A1 | 3/2007 | Esch et al. |
| 2008/0281314 A1 | 11/2008 | Johnson et al. |
| 2012/0029501 A1 | 2/2012 | Prakash et al. |
| 2012/0110834 A1 | 5/2012 | Smith et al. |
| 2012/0123403 A1 | 5/2012 | Brannan |
| 2012/0203218 A1 | 8/2012 | Bonn |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| EP | 2 098 184 | 9/2009 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| GB | 2 434 872 | 8/2007 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO00/36985 | 6/2000 |
| WO | WO00/49957 A | 8/2007 |
| WO | WO2010/035831 | 4/2010 |

OTHER PUBLICATIONS

U.S. Appl. No. 08/483,742, filed Jun. 7, 1995, Roger A. Stern.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,307, filed May 22, 2012, Casey M. Ladtkow.
U.S. Appl. No. 13/477,320, filed May 22, 2012, Joseph D. Brannan.
U.S. Appl. No. 13/483,858, filed May 30, 2012, Francesca Rossetto.

U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed Jul. 2, 2012, Steven P. Buysse.
U.S. Appl. No. 13/539,725, filed Jul. 2, 2012, Steven P. Buysse.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Caurs et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., Theoretical Aspects of "Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite-Element Codes to Model Electrical Heating and Non•Llnear Thermal Transport in Biological Media", Proc. ASME HTD-355, 131 (1997).
Ian D. McRury et al., the Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, p. 140 (Abstr).

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Int'l Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157

"Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817•825.

Urologix, Inc.—Medical Professionals: Targis™ Technology (Date Unknown). "Overcoming the Challenge" located at: <http://www.urologix.com!medicaUtechnology.html > Nov. 18, 1999; 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation—'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.

European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.

European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.

European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended d6ted Jul. 6, 2011.
European Search Report EP 11004942 dated Oct. 4, 2011.
European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12165136 dated Jun. 13, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

MICROWAVE ANTENNA ASSEMBLY HAVING A DIELECTRIC BODY PORTION WITH RADIAL PARTITIONS OF DIELECTRIC MATERIAL

CROSS-REFERENCE TO RELATED PATENT APPLICATIONS

The present application is a Continuation of U.S. patent application Ser. No. 12/197,405, filed on Aug. 25, 2008, the entire content of which is hereby incorporated by reference.

BACKGROUND

1. Technical Field

The present disclosure relates generally to microwave antenna assemblies that can treat tissue. More particularly, the present disclosure is directed to a microwave antenna assembly having a dielectric body portion with radial partitions of dielectric material for directing energy to treat tissue.

2. Background of Related Art

Treatment of certain diseases requires destruction of malignant tissue growths (e.g., tumors) or surrounding tissue. It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat, ablate and/or coagulate tissue. Microwave energy is sometimes utilized to perform these methods. In particular, microwave energy is used to coagulate or ablate tissue. Another method used to treat diseased tissue is to resect a portion of the diseased organ, tissue or anatomical structure. For example, a liver may contain diseased tissue and healthy tissue. One treatment option is to ablate some of the liver tissue to resect a portion of the liver including the diseased tissue.

Microwave energy may be applied via antenna assemblies that can penetrate tissue. There are several types of antenna assemblies, such as monopole and dipole antenna assemblies. In monopole and dipole antenna assemblies, most of the microwave energy radiates perpendicularly away from the axis of the conductor. A monopole antenna assembly includes a single, elongated conductor that transmits the microwave energy. A typical dipole antenna assembly has two elongated conductors parallel to each other and positioned end-to-end relative to one another with an insulator placed therebetween. Each of the conductors is typically about ¼ of the length of the wavelength of the microwave energy making the aggregate length of both conductors about ½ of the wavelength of the microwave energy.

A coaxial dipole antenna assembly typically includes a first elongated conductor and a second elongated conductor disposed concentrically around the first elongated conductor along about half of the distance of the coaxial assembly. The portion having the second elongated conductor is about ¼ of a wavelength and the portion having only the first elongated conductor is also about ¼ of a wavelength, making the aggregate length of the antenna assembly about a ½ wavelength. By selecting the microwave energy wavelength to be twice the length of the dipole, power is more efficiently transmitted from the antenna assembly to the surrounding tissue.

Some microwave antenna assemblies have a narrow operational bandwidth, a wavelength range at which operational efficiency is achieved, and hence, are incapable of maintaining a predetermined impedance match between the microwave delivery system (e.g., generator, cable, etc.) and the tissue surrounding the microwave antenna assembly. More specifically, as microwave energy is applied to tissue, the dielectric constant of the tissue immediately surrounding the microwave antenna assembly decreases as the tissue is heated. This drop may cause the optimal microwave energy wavelength to change beyond the bandwidth of the antenna. As a result, there may be a mismatch between the bandwidth of conventional microwave antenna assemblies and the microwave energy being applied.

SUMMARY

The present disclosure relates generally to microwave antenna assemblies that can treat tissue. More particularly, the present disclosure is directed to a microwave antenna assembly having a dielectric body portion with radial partitions of dielectric material for treating tissue by coagulating, dissecting, melting, ablating or affecting the tissue.

In one embodiment of the present disclosure, a microwave antenna assembly includes first and second elongated conductors, and a dielectric body portion. The first elongated conductor is associated with a first radiating portion at least partially along the length thereof. A second elongated conductor is disposed within the first elongated conductor and is associated with a second radiating portion at least partially along the length thereof. The dielectric body portion is disposed along the length of at least one of the first and second elongated conductors and the dielectric body portion includes two or more radial partition of dielectric material having difference dielectric constants. The geometry, density, and/or dielectric material may be selected to shape a radiation pattern radiating from the first radiating portion.

In another embodiment of the present disclosure, the one or more radial partitions of dielectric material include first and second radial partitions of dielectric material, wherein the dielectric constant of the first radial partition is greater than the dielectric constant of the second radial partition.

The first elongated conductor may include a lumen therethrough and the second elongated conductor is at least partially disposed within the lumen of the first elongated conductor to form a coaxial dipole antenna assembly. The second elongated conductor may be at least partially disposed within the lumen such that a portion thereof is a first distance from the longitudinal axis of the first elongated conductor.

In another embodiment of the present disclosure, a radial partition of dielectric material of the one or more radial partitions of dielectric material includes a hollow chamber. The hollow chamber may include one or more of water, air, gas or a vacuum disposed therein and these materials may be mechanically pumped in or out by one or more ways known in the art. One of the first and second elongated conductors may include first and second conductivity regions. The first conductivity region has a first electrical conductivity and the second conductivity region has a second electrical conductivity being different from the first electrical conductivity.

In another embodiment of the present disclosure, two or more dielectric materials form four radial partitions of dielectric material. Each of the four radial partitions of dielectric material are different from each radially adjacent radial partition of the four radial partitions. For example, two radial partitions may be positioned to form a first opposing pair of radial partitions and two radial partitions are positioned to form a second opposing pair of radial partitions of dielectric material. The four radial partitions form an equal angle quadrant of radial partitions. The dielectric constant of the first opposing pair of radial partitions is greater than the dielectric constant of the second opposing pair of radial partitions creating a specific radiation effect. In one embodiment, the dielectric constant of the first opposing pair of radial partitions is about two to about twenty times greater than the dielectric constant of the second opposing pair of radial partitions.

In another embodiment of the present disclosure, the two radial partitions of dielectric material form the dielectric body portion. The dielectric constant of the dielectric material of the first radial partition is from about 10 to about 100 and the dielectric constant of the dielectric material of the second radial partition is from about 2 to about 5 creating a specific radiating effect.

In another embodiment of the present disclosure, the dielectric body portion is rotatable about the longitudinal axis of the first elongated conductor. An angle sensor may be configured to determine an angle of rotation of the dielectric body portion about the longitudinal axis relative to the first elongated conductor.

In yet another embodiment, the microwave antenna assembly includes a second dielectric body portion at least partially disposed about the second elongated conductor. The second dielectric body portion includes two or more radial partitions of dielectric material disposed along the length of the second elongated conductor; the dielectric material of the two or more radial partitions being different. The first dielectric body portion causes the first radiating portion to have a first radiation pattern and the second dielectric body portion causes the second radiating portion to have a second radiation pattern. Each of the first and second radiation patterns has one or more elongated radiation lobes.

In still another embodiment of the present disclosure, an electrosurgical system for treating tissue includes an electrosurgical generator for generating microwave energy and an antenna assembly. The antenna assembly includes first and second elongated conductors, and a dielectric body portion as described in one of the embodiments above.

The electrosurgical generator includes an S-parameter sensor configured to determine one or more S-parameters of the antenna assembly. The first dielectric body portion causes the first radiating portion to have a radiation pattern including one or more elongated radiation lobes. The one or more elongated radiation lobe is rotatable about the longitudinal axis of the first elongated conductor. The electrosurgical generator associates each determined S-parameter with a determined angular direction of the one or more elongated radiation lobes.

In another embodiment, the electrosurgical generator generates an interrogation signal and the S-parameter sensor determines one or more S-parameters of the antenna assembly utilizing the interrogation signal. The interrogation signal may include a plurality of wavelengths such that the electrosurgical generator associates each determined S-parameter to a wavelength of the plurality of wavelengths. For example, in one embodiment of the one or more S-parameters may include a S11 parameter.

In yet another embodiment, the microwave antenna assembly also includes an angle sensor in operative communication with the electrosurgical generator. The angle sensor determines an angle of rotation of the one or more elongated radiation lobes about the longitudinal axis of the first elongated conductor. The angle sensor communicates the determined angle of rotation to the electrosurgical generator. Additionally or alternatively, the electrosurgical generator associates each determined S-parameter to the determined angle of rotation (from the angle sensor) of the one or more elongated radiation lobe.

BRIEF DESCRIPTION OF THE DRAWINGS

Various embodiments are described herein with reference to the drawings wherein.

DETAILED DESCRIPTION

Figure 1:
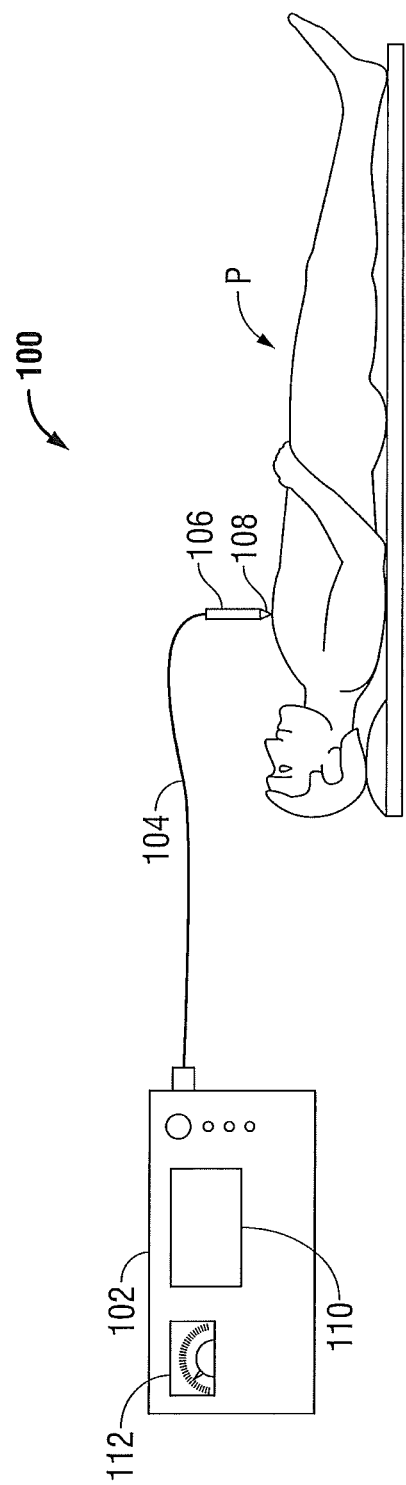
FIG. 1 is a schematic diagram of a microwave electrosurgical system for treating tissue in accordance with an embodiment of the present disclosure.

Referring to the drawings, FIG. 1 is a schematic diagram of an electrosurgical system 100 for treating tissue using microwave energy. Electrosurgical system 100 includes an electrosurgical generator 102 electrically coupled to a cable 104 that can guide microwave energy to a surgical instrument 106. Surgical instrument 106 includes an antenna assembly 108 that can treat tissue of patient P. Surgical instrument 106 may include other antenna assemblies (not shown).

Electrosurgical generator 102 includes graphical user interface 110 and dial indicator 112. Electrosurgical generator 102 may also include other input or output devices such as knobs, dials, switches, buttons, displays and the like for control, indication and/or operation. Surgical instrument 106 may include buttons (not shown) to communicate to electrosurgical generator 102 to generate the microwave energy. Electrosurgical system 100 may also include a footswitch (not depicted) that connects to electrosurgical generator 102. When actuated, the footswitch can cause electrosurgical generator 102 to generate the microwave energy. Utilizing buttons on surgical instrument 106 or a footswitch enables the surgeon to activate the microwave energy while remaining near patient P regardless of the location of electrosurgical generator 102.

Figure 2:
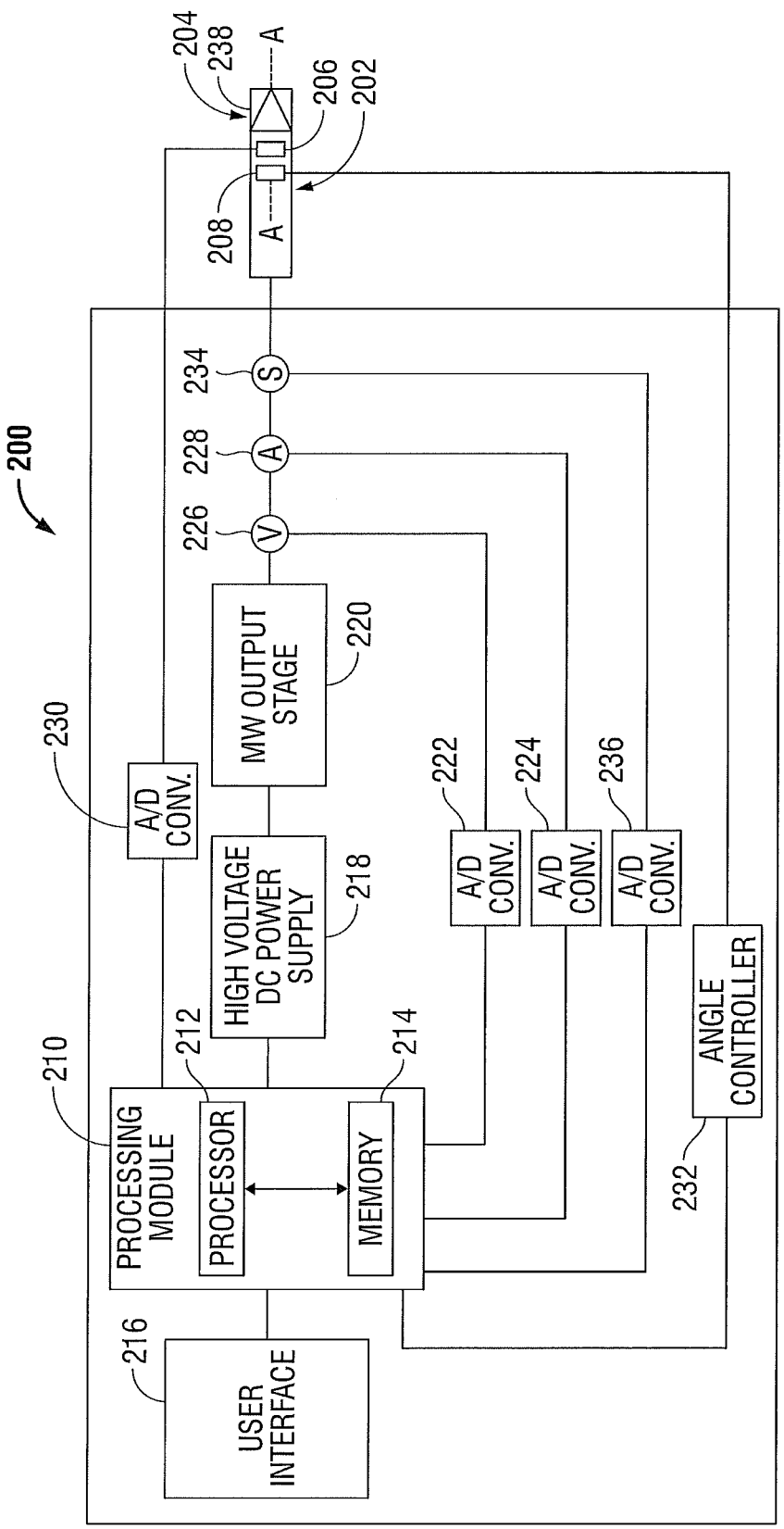
FIG. 2 is a block diagram of a electrosurgical generator that can generate microwave energy for ablating tissue in accordance with an embodiment of the present disclosure.

Referring to the drawings, FIG. 2 is a block diagram of an electrosurgical generator 200 that can generate microwave energy to treat tissue. Electrosurgical generator 200 of FIG. 2 may be similar to or identical to electrosurgical generator 102 of FIG. 1. Electrosurgical generator 200 may be implemented wholly or partially in hardware, software, software in execution, bytecode, microcode, firmware, circuitry or some sufficient combination. Electrosurgical generator 200 may be connected to a network (e.g., the internet) and may include digital or analog connection devices, such as an RS-232 connection, an Ethernet connection or a GPIB connection.

Electrosurgical generator 200 is connected to a surgical instrument 202 which includes an antenna assembly 204 configured to ablate tissue for resection or other surgical purposes. Antenna assembly 204 may form part of multiple antenna assemblies (not shown) in a parallel row of antenna assemblies to create an ablation plane for resection procedures (e.g., a "picket fence" ablation plane). Antenna assembly includes dielectric body portion 238.

Electrosurgical generator 200 is controlled by processing module 210 having a processor 212 and memory 214. Processor 212 may be a microprocessor, a microcontroller, logic circuitry or a semiconductor-based logic device. Memory 214 may include program data, variables, stacks, heaps and the like. Processing module 210 may include communication interfaces such as serial bus interface or a parallel bus interface, and may also include related I/O buffers, flags or associated circuitry. Additionally, processing module 210 may include analog-to-digital converters and/or digital-to-analog converters.

Processing module 210 is in operative communication with user interface 216 and can receive user data therefrom. User interface 216 may include mechanical or electrical interfaces, such as footswitches, switches, dials, screens, touch screens, speakers, microphones or the like, and associated circuitry. Processing module 210 is in operative communication with high voltage DC power supply 218 receives instructions from processing module 210 to supply the microwave output stage 220 with sufficient power. Processing module 210 may control microwave output stage 220 directly (not depicted) or indirectly through high voltage DC power supply 218. Microwave output stage 220 may output microwave energy having a single wavelength, a plurality of wavelengths or a spectrum of wavelengths. The effective wavelength of antenna assembly 204 may differ and may change based upon the surrounding tissue type, the surrounding tissue condition and/or the current progression of the ablation procedure. Microwave output stage 220 may change a wavelength of the microwave energy to "track" or "match" an effective wavelength of antenna assembly 204. High voltage DC power supply 218 provides the power for microwave output stage 220 while processing module 210 controls the "on/off" times and/or the duty cycle. Processing module 210 utilizes one or more modulation techniques to control the microwave energy, e.g., a pulse-width modulation technique. Alternatively, processing module 210 may send a digital code to another semiconductor device (not shown), such as an ASIC chip, which generates the waveform for controlling high voltage DC power supply 218.

Processing module 210 may utilize feedback to control the generation of microwave energy, such as feedback from analog-to-digital (referred to herein as "A/D") converters 222 and 224. A/D converter 222 converts voltage data from voltage sensor 226 to digital voltage data and A/D converter 224 converts current data from current sensor 228 to digital current data. Processing module 210 may also use the voltage and/or current data to control the generation of the microwave energy. For example, processing module 210 may implement a feedback type control algorithm using the digital and current data as "error" (such as in a PID algorithm) to determine what adjustments to make to the generated microwave energy.

Figure 3A:
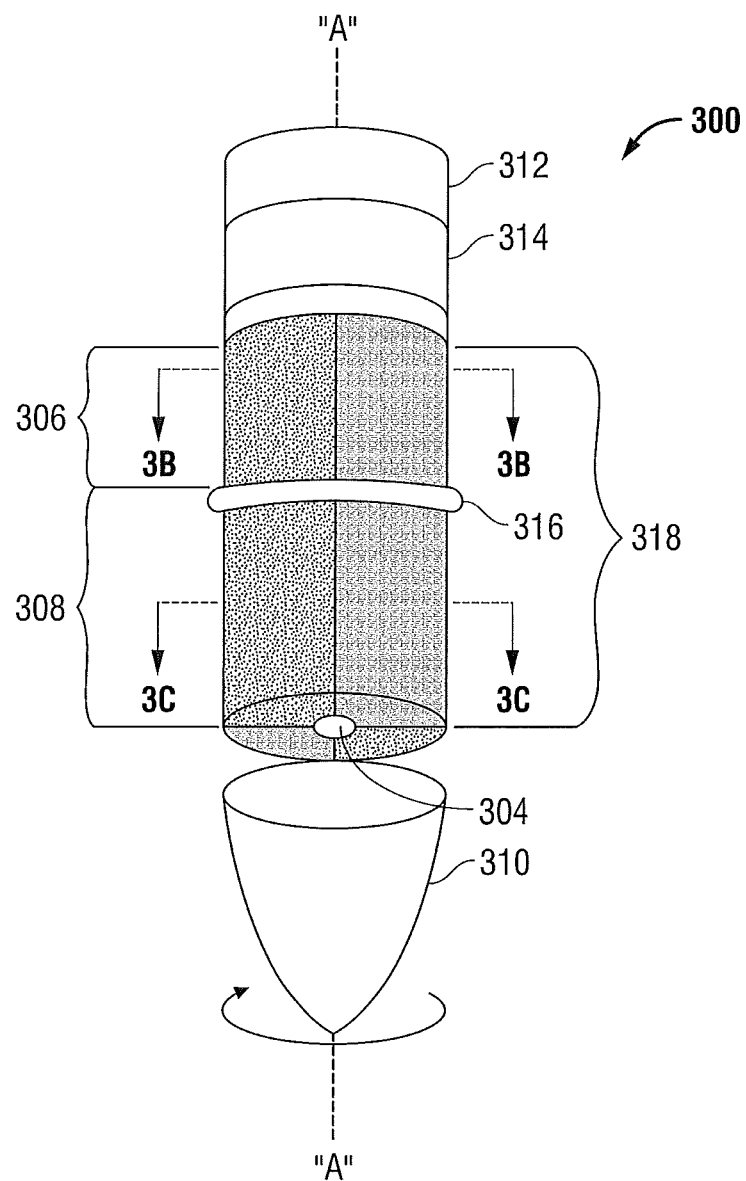
FIG. 3A is a schematic, perspective view of an antenna assembly that has a dielectric body portion having four radial partitions of dielectric material disposed around the radiating portions of the antenna assembly in accordance with an embodiment of the present disclosure.
Figure 3B:
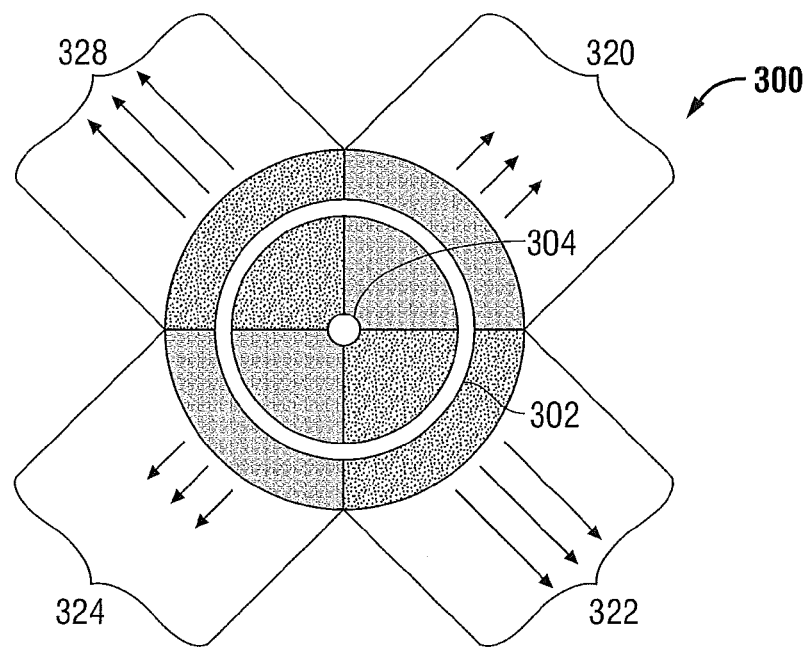
FIG. 3B is a cross-sectional view of the antenna assembly of FIG. 3A along a proximal radiating portion with illustrative electric field lines in accordance with an embodiment of the present disclosure.
Figure 3C:
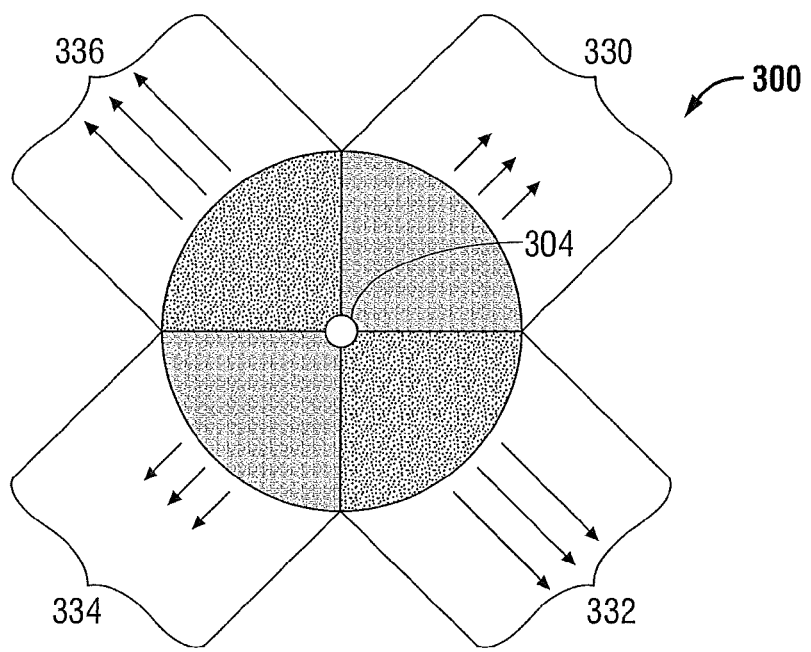
FIG. 3C is a cross-sectional view of the antenna assembly of FIG. 3A along a distal radiating portion with illustrative electric field lines in accordance with an embodiment of the present disclosure.

Referring to FIGS. 3A, 3B, and 3C, an antenna assembly 300 is shown that includes a first conductor 302 (only shown in FIG. 3B) and second conductor 304. The first conductor 302 defines a lumen (not shown) in which second conductor 304 is disposed therein, e.g., first conductor 302 concentrically surrounds at least partially second conductor 304. Antenna assembly 300 also includes a first radiating portion 306 and a second radiating portion 308. Antenna assembly 300 is attached to a coaxial cable 312 and may include a choke 314. A puck 316 may form a spacer between the two radiating portions 306 and 308.

First conductor 302 and/or second conductor 304 may be made of a suitable conductive metal and may be semi-rigid or flexible, such as, for example, copper, gold, stainless steel or other conductive metals with similar conductivity values. Metals may be selected based on a variety of factors, such as conductivity and tensile strength. Although stainless steel has lower conductivity than copper and/or gold, stainless steel in some instruments may provide the necessary strength required to puncture tissue and/or skin. In such cases, the first conductor 302 and/or the second conductor 304 (or portions thereof) may be plated with a conductive material (e.g., copper, gold, etc.) to improve conductivity and/or decrease energy loss.

Additionally or alternatively, the first conductor 302 and/or the second conductor 304 may have varying regions of electrical conductivity to shape the radiation pattern, e.g., first conductor 302 and the second conductor 304 may include higher electrical conductivity regions to enhance the directionality of the electric field lines radiating therefrom. For example, first conductor 302 and/or the second conductor 304 may be coated with or have higher electrical conductivity values adjacent to regions having higher dielectric constants or vice versa. Also, first conductor 302 and/or the second conductor 304 may have a hollow core, different skin coating depths, one or more hollow portions, may have thicker or thinner coatings relative to each other, may be thicker or thinner relative to each other, and/or have different geometries to further affect the directionality of the radiation lobes.

As mentioned above, it is envisioned that second conductor 304 may be configured to pierce or slice through tissue, either mechanically and/or with the aid of RF or microwave energy. In the embodiment where second conductor 304 can mechanically pierce or slice through tissue, antenna assembly 300 may be configured thin enough to pierce or slice through tissue upon the exertion of a predetermined amount of force. Additionally or alternatively, second conductor 304 may be configured to receive RF or microwave energy and transmit that energy to tissue to piece or slice through tissue or assist in piercing or slicing through tissue. Second conductor 304 may also include a tapered end 310 and may be formed from a variety of heat-resistant materials suitable for penetrating tissue, such as metals (e.g., stainless steel), ceramics such as glass ceramics, and various thermoplastic materials, such as poletherimide, polyamide thermoplastic resins, an example of which is Ultem® sold by General Electric Co. of Fairfield, Conn.

Referring now to FIGS. 3B and 3C, two cross sectional views along lines 3B-3B of FIG. 3A and along lines 3C-3C of antenna assembly 300 of FIG. 3A are shown, respectively. Dielectric body portion 318 may be configured to shape and/or control the radiation pattern radiating from first radiating portion 306 and second radiating portion 308. In the representative FIG. 3A embodiment, dielectric body portion 318 has four radial partitions of dielectric material, each having the same fraction of the total radial area (dielectric body portion 318 has equal angle quadrants of radial partitions). For example, FIG. 3B shows a cross-sectional view of dielectric body portion 318 along the first radiating portion 306, which includes four radial partitions of a dielectric material, namely, radial partitions 320, 322, 324, and 328. FIG. 3C shows four radial partitions of the dielectric material, namely, radial partitions 330, 332, 334 and 336.

Radial partitions 328, 322, 336 and 332 have a material of greater dielectric constant than radial partitions 320, 324, 330 and 334 or vice versa. The difference in the dielectric constants produces different electric fields lines around the radial partitions of the dielectric body portion 318. The electric field lines are illustrated in FIGS. 3B and 3C, which show elongated radiation lobes 338 and 340 being emitted from radiating portions 306 and 308 (see FIG. 3A), respectively, with side radiation lobes 342 and 344 (see also FIG. 3D). The elongated radiation lobes are the result of the higher dielectric constant of radial portions 328, 322, 336 and 332 relative to 320, 324, 330 and 334. A low dielectric material may have a dielectric constant from about 2 to about 10. Examples of low dielectric materials include low dielectric ceramics (e.g., glass ceramics) or polymers. Additionally, a high dielectric constant may be a dielectric constant from about 10 to about 100. Examples of high dielectric materials include high dielectric ceramics (e.g., glass ceramics) or polymers. It is envisioned that the electric field saturation limits of these dielectrics will not be reached by the microwave energy.

By regulating the dielectric constant of the various radial partitions, different radiation patterns are possible for different tissue types. For example, the higher dielectric partitions may have a dielectric constant from about 5 to about 20 times the dielectric constant of the lower dielectric partitions. Moreover, and as explained below, the geometric shape, thickness and density of the partitions will also affects the shape, size and intensity of the radiation lobes. For example, thicker dielectrics may cause a greater elongation of the elongated radiation lobes (also referred to as "beams").

In another embodiment, the radial partitions 320-328 and 330-336 may be formed by hollow chambers and the dielectric materials may be water and/or air. Water has a dielectric constant of about 80, while air and a vacuum have a dielectric constant of about 1 which will create a particular radiating pattern with elongated lobes. Rotation of the dielectric body portion 318 along axis A-A (see FIG. 3A) in this embodiment may form a particular radiation pattern with elongated lobes.

Referring again to FIG. 3B, radial partitions 320-328 of dielectric material are disposed about first conductor 302 and radial partitions 320-328 of dielectric material are also disposed within first conductor 302. By having offset dielectric constants between the inside or outer dielectric materials disposed relative to first conductor 302 different radiating fields may be generated and the radiation pattern may be tuned for a particular purpose. Additionally, by offsetting second conductor 304 from the central axis of first conductor 302 (not depicted) the directionality of the radiation pattern may be enhanced or tuned for a particular purpose. Moreover, when elongated conductors 302 and 304 have different shapes or dimensions (not depicted), dielectric body portion 318 may be configured to include thicker and thinner regions (or different dielectric material with different densities) along the longitudinal axis A-A of dielectric body portion 318 to vary the radiation pattern.

Figure 3D:
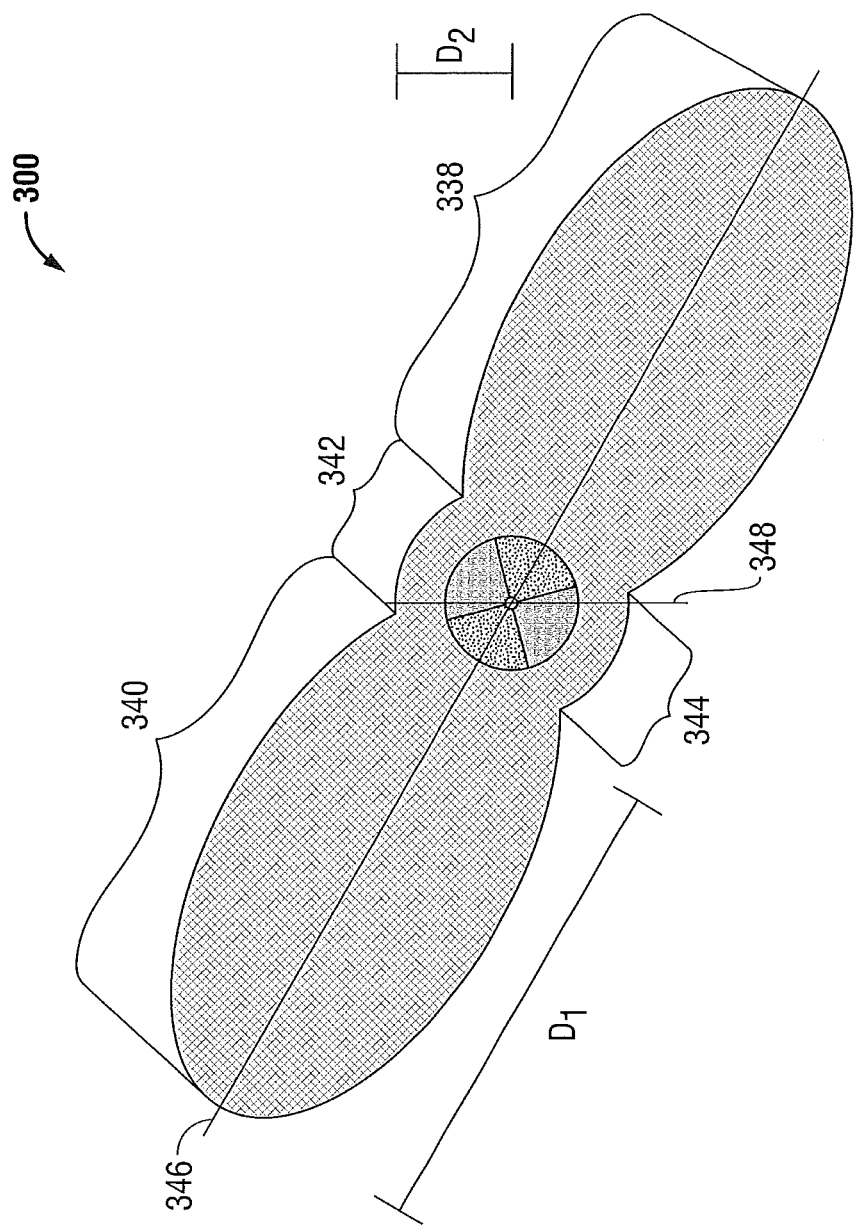
FIG. 3D is a cross-sectional view of the antenna assembly of FIG. 3A along the distal radiating portion illustrating a radiation pattern having two elongated radiation lobes in accordance with an embodiment of the present disclosure.

FIG. 3D shows another antenna assembly 300 with an illustrative radiation pattern. The radiation pattern includes elongated radiation lobes 338 and 340 and side radiation lobes 342 and 344. The radiation pattern corresponds to the strength of the microwave energy in a given direction. For example, axis 346 and axis 348 are shown. The radiation pattern extending from antenna assembly 300 to the end of the radiation pattern along axis 346 is depicted by distance D1. Likewise, the radiation pattern extending from antenna assembly 300 to the end of the radiation pattern along axis 348 is depicted by a distance D2. The different distance values of D1 compared to D2 correspond to different microwave energy power levels. The power level changes as the radial angle of antenna assembly 300 changes. The geometry, density and the dielectric material making up the dielectric body portion 318 may be configured to shape the radiation pattern, e.g., to create wide or narrow ablation areas. Narrow ablation radiation lobes may enhance surgical instruments using "picket fence" antenna assemblies during a resection procedure by increasing the effective distance between the antenna assemblies so that they may be spaced greater than 1.0 cm apart.

Figures 4, 5:
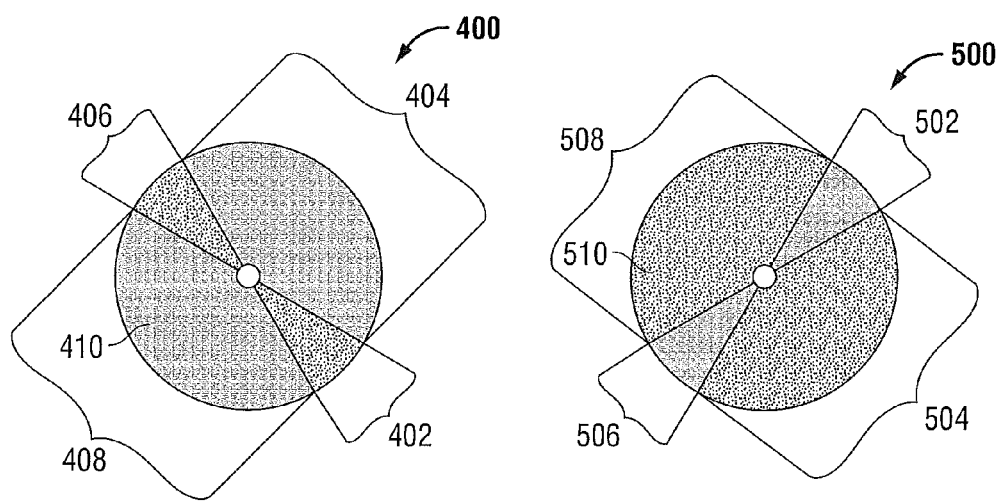
FIGS. 4-7 are cross-sectional views along the distal radiating portion of additional embodiments of the antenna assembly in accordance with an embodiment of the present disclosure.

Referring now to FIGS. 4 and 5, two cross-sectional views of antenna assemblies 400 and 500 are shown, respectively. Antenna assemblies 400 and 500 are configured to radiate two elongated radiation lobes. Antenna assembly 400 includes a dielectric body portion 410 having opposing radial partitions 402 and 406 having a higher dielectric constant and opposing radial partitions 404 and 408 having a lower dielectric constant. The microwave energy will radiate and favor radial partitions 402 and 406 because of the higher dielectric constant resulting in narrow elongated radiation patterns similar to FIG. 3D.

Antenna assembly 500 includes dielectric body portion 510 having opposing radial partitions 504 and 508 having a higher dielectric constant and opposing radial partitions 502 and 506 having a lower dielectric constant. The microwave energy will radiate and favor radial partitions 504 and 508 because of the higher dielectric constant resulting in wider elongated radiation patterns than antenna assembly 400 (see FIG. 4).

Antenna assemblies 400 and 500 are geometrically dissimilar. The dielectric material type, density, thickness and the dielectric constant of the material(s), all affect the radiation pattern and associated radiation lobes. For example, and based on geometry alone, the radiation pattern of antenna assembly 400 should have narrower radiation lobes than that of antenna assembly 500 because of the geometric difference between the dielectric materials. However, dielectric density, dielectric thickness, variations in the dielectric materials and differences in the relative dielectric ratios, all affect the effective impedance of the antenna and the resulting radiation pattern, which may be partially compensated for by adjusting the length of the antenna assembly.

Figures 6, 7:
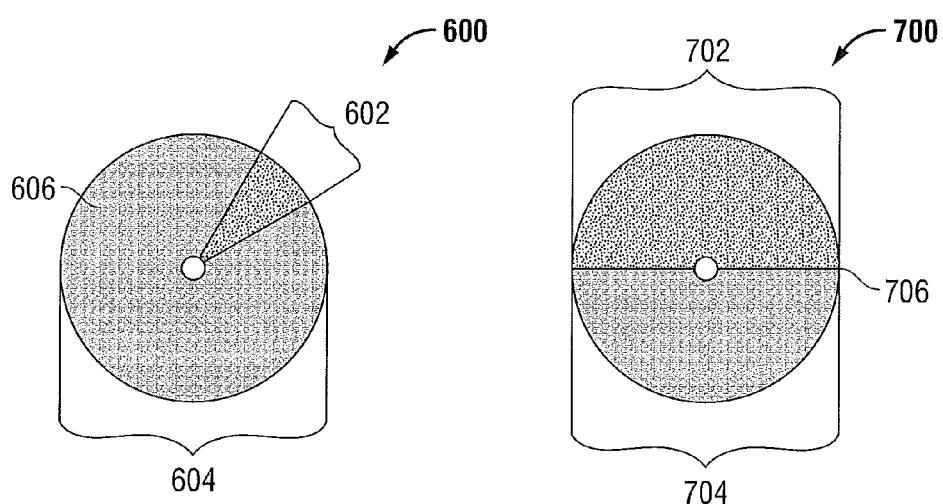

Referring to FIGS. 6 and 7, antenna assemblies 600 and 700 are shown, respectively. Antenna assembly 600 includes dielectric body portion 606 having radial partitions 602 and 604, 602 having the higher dielectric constant. Antenna assembly 700 includes radial partitions 702 and 704, wherein radial partition 702 has the higher dielectric constant. Antenna assemblies 600 and 700 will generate radiation patterns with a single elongated radiation lobe on one side of the antenna assembly with similar side lobes on opposite sides on the assembly. Antenna assembly 600 has a lower fraction of higher dielectric material versus lower dielectric material compared to antenna assembly 700. The lower fraction of antenna assembly 600 will tend to form a more narrow elongated radiation lobe than that of antenna assembly 700.

From the foregoing and with reference to the various figure drawings, those skilled in the art will appreciate that certain modification can also be made to the present disclosure without departing form the scope of the same, for example, referring again to FIG. 2, antenna assembly 202 may be rotatable about axis A-A such that any elongated radiation lobes rotates therewith. As mentioned above, the dielectric body portion 238 may be configured to cause the radiation pattern of surgical instrument 202 to have at least one elongated radiation lobe. Angle sensor 206 communicates an angle of rotation to electrosurgical generator 202. Electrosurgical generator 200 utilizes angle sensor 206 and actuator 208 to determine one or more parameters of the applied microwave energy based upon the angle of the elongated radiation lobe(s). Electrosurgical generator 200 may control the rotation of antenna assembly 202 by communicating a control signal from angle controller 232 to antenna assembly 202. Additionally or alternatively, antenna assembly 202 may be rotated using a mechanical linkage, a hydraulic system, a magnetic system, a motorized system, an energizable system, a user-activated knob or switch in the handle of surgical instrument 303 and/or on electrosurgical generator 200, or the like.

For example, electrosurgical generator 200 may include A/D converter 230 that converts analog angle-of-rotation data from angle sensor 206 to digital angle sensor data that is communicated to processing module 210. Processing module 210 can send instructions to angle controller 232 to control the angle of rotation utilizing actuator 208. Electrosurgical generator 200 may also include an S-parameter sensor 234 which communicates analog S-parameter data to A/D converter 236 which converts the data to digital S-parameter data such that processing module 210 can process the data.

S-parameter sensor 234 can determine one or more S-parameters. Because S-parameters are frequency dependant and tissue characteristics dependant, electrosurgical generator 200 can associate each determined S-parameter with an angle of rotation as received from angle sensor 206 and/or can associate each determined S-parameter with a frequency (or wavelength) generated by MW output stage 220. Additionally, the dielectric body portion 238 facilitates a non-isotropic radiation pattern with one or more elongated nodes causing the S-parameter to be more strongly dependant upon the angle (e.g., the angular direction or angle of rotation) of the elongated radiation node or nodes. One type of S-parameter is a S11 parameter, which is related to reflected microwave energy and/or scattered microwave energy. S-parameters are also affected by the dielectric constant of the surrounding tissue.

Electrosurgical generator 200 may be configured to perform an angular sweep by using angle controller 232 to control an angle of rotation of the dielectric body portion 238 of antenna assembly 204 and/or control the angle of rotation of wholly antenna assembly 204 while applying microwave energy. The S-parameters determined may be associated with an angle of rotation to identify a tumor or anatomical structure. For example, if antenna assembly 204 were inserted into lung tissue near a tumor, the characteristic of the tumor may result in different S-parameters as compared to lung tissue and/or the surrounding air. Therefore, an angular sweep may be used to determine the angle of rotation for antenna assembly 204 when applying therapeutic microwave energy.

Electrosurgical generator 200 may also utilize the determined S-parameters during an angular sweep to determine the completeness of the ablation as a function of the angle of rotation and/or the wavelength. Additionally, the S-parameters may be utilized by electrosurgical generator 200 during the angular sweep to determine the overall proximity to vessels or other tissue, the consistency of the ablation radius, the ablation shape, the homogeneity of the surrounding tissue, the antenna coupling and/or the tissue hydration of the surrounding tissue. The rate of rotation may have a maximum rate of rotation from about 6 to about 10 seconds per 360 degrees of rotation.

Additionally or alternatively, the MW output state 220 may utilize an interrogation signal. The interrogation signal may have the same frequency as that of the therapeutic microwave energy (e.g., 915 MHZ) or may have a plurality of frequencies (or wavelengths), such as from 500 MHZ to about 3 GHZ, forming a broadband interrogation signal. A broadband interrogation signal may better reflect antenna coupling to tissue, which is related to tissue hydration. The interrogation signal may occur intermittently while applying therapeutic microwave energy and/or may occur as an initial pulse. An intermittent interrogation signal may occur every minute in a 10-minute procedure and every 10 to 20 seconds during a 3-minute procedure. S-parameter sensor 234 may determine an S-parameter for each of the several wavelengths. Electrosurgical generator 200 may associate each S-parameter with a wavelength (or frequency) as measured during the interrogation signal.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system for treating tissue, the system comprising:
    an electrosurgical generator configured to generate microwave energy; and
    an antenna assembly configured to radiate the microwave energy, the antenna assembly comprising:
        a first elongated conductor associated with a first radiating portion at least partially along the length thereof;
        a second elongated conductor disposed within the first elongated conductor and associated with a second radiating portion at least partially along the length thereof; and
        a dielectric body portion disposed along the length of at least one of the first elongated conductor and the second elongated conductor, the dielectric body portion including at least two radial partitions of dielectric material having different dielectric constants, wherein the electrosurgical generator includes an S-parameter sensor configured to determine at least one S-parameter of the antenna assembly and wherein the first dielectric body portion causes the first radiating portion to have a radiation pattern including at least one elongated radiation lobe, wherein the electrosurgical generator associates the determined at least one S-parameter with an angular direction of the at least one elongated radiation lobe.

2. The electrosurgical system according to claim 1, wherein the at least one elongated radiation lobe is rotatable about a longitudinal axis of the first elongated conductor.

3. The electrosurgical system according to claim 2, wherein the microwave antenna assembly further comprises:
    an angle sensor in operative communication with the electrosurgical generator, the angle sensor configured to determine at least one angle of rotation of the at least one elongated radiation lobe about the longitudinal axis of the first elongated conductor, the angle sensor configured to communicate the determined at least one angle of rotation to the electrosurgical generator.

4. The electrosurgical system according to claim 3, wherein the electrosurgical generator associates each determined S-parameter of the at least one S-parameter with one of the determined at least one angle of rotation of the at least one elongated radiation lobe.

5. The electrosurgical system according to claim 3, wherein the electrosurgical generator generates an interrogation signal and the S-parameter sensor determines the at least one S-parameter of the antenna assembly utilizing the interrogation signal.

6. The electrosurgical system according to claim 5, wherein the interrogation signal includes a plurality of wavelengths and the electrosurgical generator associates each determined S-parameter of the at least one S-parameter to a wavelength of the plurality of wavelengths.

7. An electrosurgical system, the system comprising:
   an electrosurgical generator configured to generate microwave energy; and
   an antenna assembly including a first conductor circumferentially disposed around a second conductor and a dielectric body portion disposed along a length of at least one of the first conductor and the second conductor, the dielectric body portion including a first set of radial partitions having a first dielectric constant and a second set of radial partitions having a second dielectric constant different than the first dielectric constant, and wherein the first and second sets of radial partitions of dielectric material include four radial partitions of dielectric material, each of the four radial partitions of dielectric material being different from each radially adjacent radial partition of the four radial partitions of dielectric material.

* * * * *